(12) United States Patent
Nowak et al.

(10) Patent No.: US 9,101,434 B2
(45) Date of Patent: Aug. 11, 2015

(54) DEVICE FOR RECORDING IMAGES OF THREE-DIMENSIONAL OBJECTS

(75) Inventors: Christoph Nowak, Vienna (AT); Horst Koinig, Klagenfurt (AT); Jurgen Jesenko, Finkenstein (AT)

(73) Assignee: A.TRON3D GMBH, Klagenfurt am Worthersee (AT)

( * ) Notice: Subject to any disclaimer, the term of this patent is extended or adjusted under 35 U.S.C. 154(b) by 625 days.

(21) Appl. No.: 13/423,351

(22) Filed: Mar. 19, 2012

(65) Prior Publication Data
US 2012/0237889 A1  Sep. 20, 2012

(30) Foreign Application Priority Data

Mar. 18, 2011 (AT) ..................... 387/2011

(51) Int. Cl.
*H04N 7/18* (2006.01)
*A62B 1/04* (2006.01)
*A61C 9/00* (2006.01)
*G01B 11/25* (2006.01)

(52) U.S. Cl.
CPC ............ *A61C 9/006* (2013.01); *G01B 11/2513* (2013.01); *A61C 9/004* (2013.01)

(58) Field of Classification Search
CPC .................. G06T 2207/30036; A61C 19/04
USPC .............................................. 348/66; 433/29
See application file for complete search history.

(56) References Cited

U.S. PATENT DOCUMENTS

| 8,411,917 B2 | 4/2013 | Gandyra | |
|---|---|---|---|
| 2003/0072011 A1* | 4/2003 | Shirley | 356/601 |
| 2010/0073461 A1 | 3/2010 | Hammes et al. | |
| 2010/0209002 A1* | 8/2010 | Thiel et al. | 382/206 |
| 2011/0001818 A1 | 1/2011 | Hur et al. | |

FOREIGN PATENT DOCUMENTS

| AT | 508 563 B1 | 2/2011 |
|---|---|---|
| DE | 9013454 U1 | 1/1992 |
| DE | 19818076 A1 | 11/1998 |
| DE | 19747061 A1 | 5/1999 |
| DE | 102007060263 A1 | 2/2009 |
| EP | 2295932 A1 | 3/2011 |
| WO | 9747942 A1 | 12/1997 |
| WO | 2009063088 A2 | 5/2009 |
| WO | 2010021972 A1 | 2/2010 |

OTHER PUBLICATIONS

Austrian Search Report dated Jan. 5, 2012, from corresponding AT application.
European Office Action, dated Feb. 12, 2014, from corresponding EP application.

* cited by examiner

*Primary Examiner* — Hung Dang
*Assistant Examiner* — Girumsew Wendmagegn
(74) *Attorney, Agent, or Firm* — Young & Thompson

(57) ABSTRACT

A device for recording images of three-dimensional objects (10), in particular teeth, has a light source (22) and a camera (32) for recording images of the object (10), whereby in the beam path of the light source (22), at least one transparent vehicle (36, 37) is arranged with a pattern that is projected onto the object (10). The vehicle (36, 37) has sections that are offset with respect to one another in the direction of the beam path. As an alternative or in addition, at least two vehicles (36, 37) can be offset with respect to one another in the direction of the beam path.

22 Claims, 4 Drawing Sheets

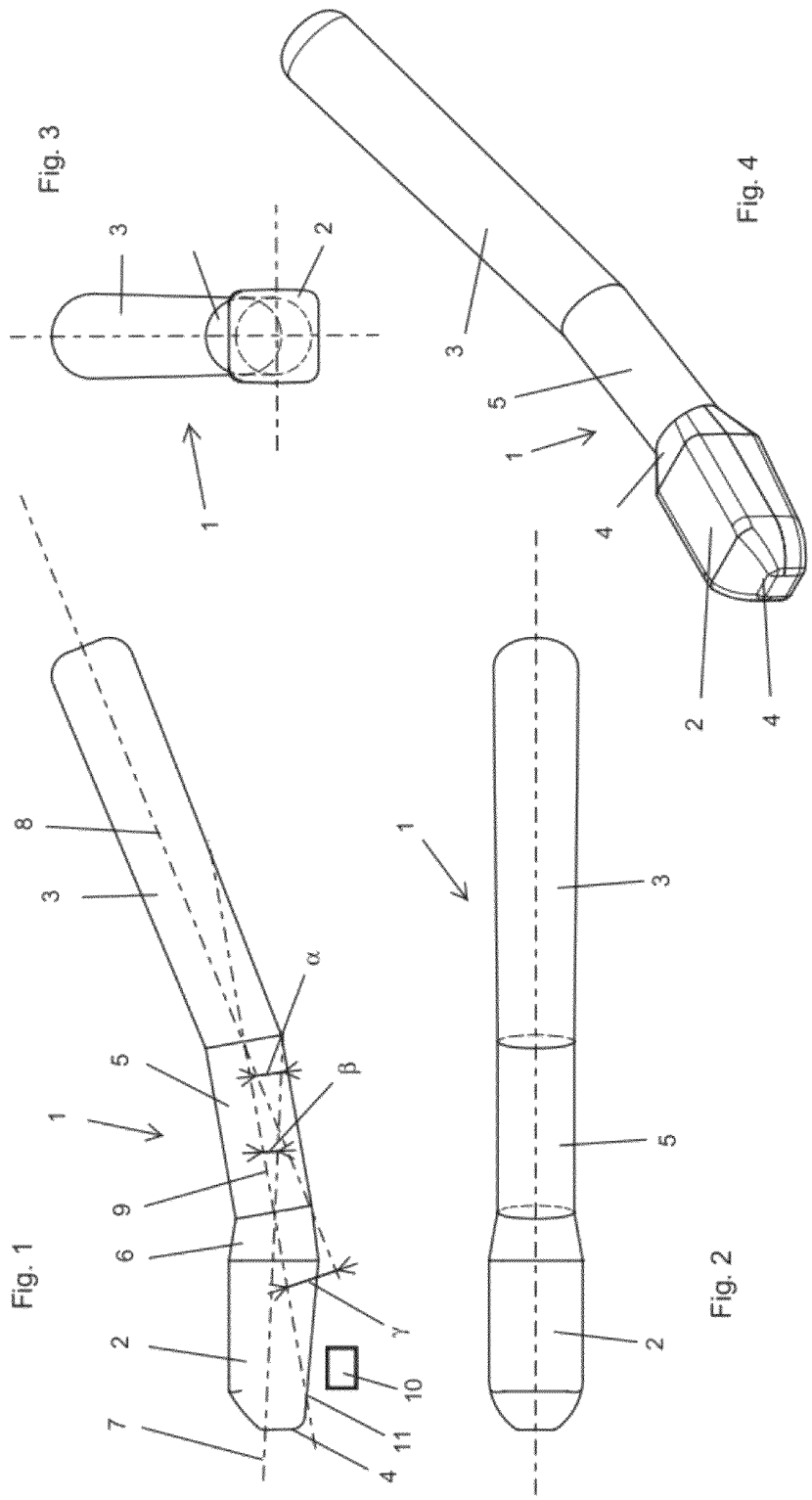

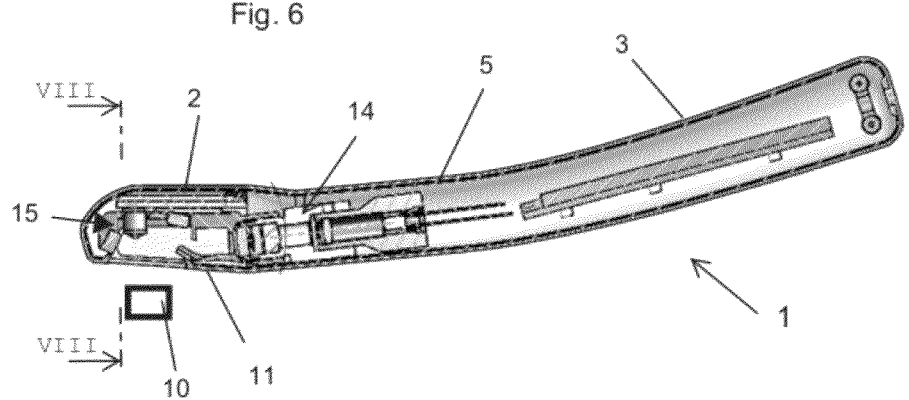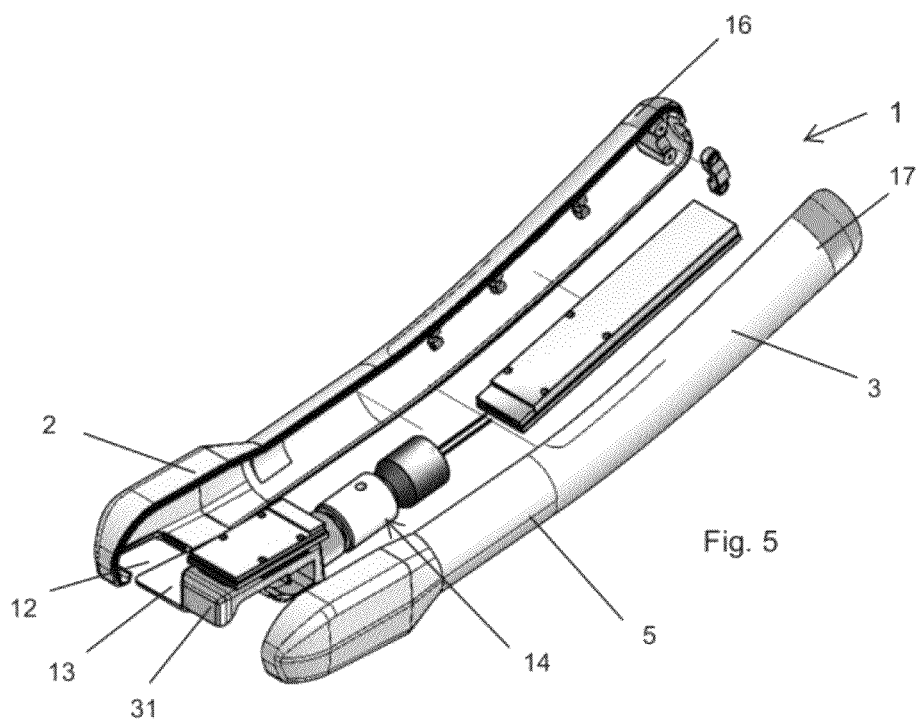

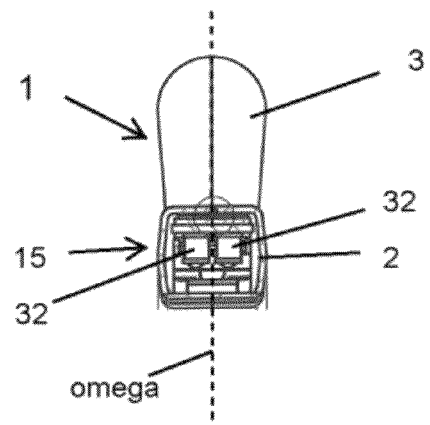
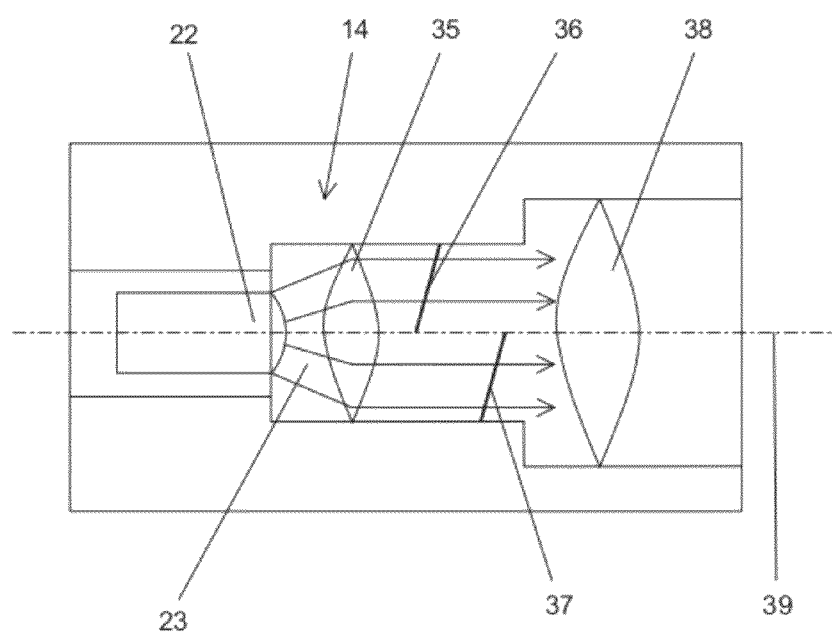

DEVICE FOR RECORDING IMAGES OF THREE-DIMENSIONAL OBJECTS

BACKGROUND OF THE INVENTION

1. Field of the Invention

The invention relates to a device for recording images of three-dimensional objects, in particular teeth, with a light source and a camera for recording images of the object, whereby in the beam path of the light source, at least one transparent vehicle is arranged with a pattern that is projected onto the object.

2. Description of the Related Art

Such devices, which are known from, for example, AT 508 563 B, are used in particular in the area of three-dimensional imaging of teeth. In this case, a pattern that is arranged according to a random principle is projected onto the object, whereby in the beam path of the light source, a transparent vehicle, e.g., a slide, is arranged with the pattern. In this case, the application extends to recording digital teeth and jaw impressions, support in diagnosis, the monitoring of dental treatments as well as the reliable monitoring of inserted implants. In addition to other uses in the field of medical and industrial technology, for example in the field of endoscopy, objects that are difficult to access can generally be measured stereometrically.

In this connection, problems exist, on the one hand, in the necessary miniaturization of the projection and imaging unit and, on the other hand, in the high requirements on the quality of the images. In particular in the field of dentistry, often dimensions of approximately 0.1-0.2 mm are relevant, so that a resolution of in the range of approximately 0.01-0.04 mm is necessary to detect all details of the objects to be imaged with sufficient resolution.

BRIEF SUMMARY OF THE INVENTION

It is therefore the object of the invention to make available a device that makes possible a precise imaging of three-dimensional objects, such as teeth.

This object is achieved with a device of the above-mentioned type, in such a way that the vehicle has sections that are offset with respect to one another in the direction of the beam path.

This object is achieved in a device of the above-mentioned type in that at least two vehicles are offset with respect to one another in the direction of the beam path.

When parts of the light beam with the pattern traverse paths of different lengths to the object to be imaged, for example since the optical center axis of the projector is tilted toward the optical center axis of the camera or since light beams are directed to the object via different mirrors, blurring of the projection of the pattern can develop on the object in the projection of the pattern that is present on a vehicle. This results in inaccuracies of the measurement.

This deviation can be compensated for according to the invention in that either individual sections of a vehicle or two or more vehicles can be offset with respect to one another in the direction of the beam path. In this way, the length of the path, which traverses the light with the pattern from the vehicle to the object, can be standardized again for the entire light beam, and thus blurriness can be reduced.

The arrangement of vehicles according to the invention is in particular advantageous when at least two mirrors in each case reflect a light beam from the light source from different directions onto the object, and a section of a vehicle or in each case a separate vehicle lies in the beam path of each light beam, since in the case of two mirrors, frequently different path lengths of the light cannot be avoided.

On the other side, the use of two mirrors is especially advantageous, however, since by the two mirrors, which reflect light from the light source from different directions onto the object, a better illumination of the objects can be made possible, or one-sided, oblique illumination of the image field on the object or tooth, which under certain circumstances is partially shadowed, e.g., in an edge area of the object itself or adjacent objects, can be avoided to a large extent, by which areas, such as, e.g., the last molar, can be easily illuminated and imaged even on the back side or can be measured subsequently.

An especially good illumination of the object for recording an image is possible when, viewed from the light source, a first mirror is behind a lens of the camera and a second mirror is in front of the lens. In this way, the object is illuminated by two opposite sides relative to the camera, so that a shadowing of the image field on the object can be reliably avoided.

When a three-dimensional image recording and, subsequently, measurement of an object is to take place, it is preferred in the invention when two cameras are provided that record images from different directions. From the state of the art, for example AT 508 563 B, a device and a method for measuring objects, such as teeth, that yield three-dimensional images are already known. This device and method, but also other known devices and methods, can be used in this invention to produce three-dimensional images.

Consequently, two cameras are provided in the invention that record images from different directions, whereby it is preferred when the cameras, viewed from the light source, lie beside one another.

When, in an embodiment of the invention, the optical axes of the mirrors lie in a plane and the lenses of the cameras are symmetric to the plane, in which the optical axes of the mirror lie, then an especially reliable illumination or image projection and image recording is possible because of this symmetrical arrangement, which results in very precise three-dimensional images, since in the measurement of edge areas (e.g., incisors), no flaws develop in the scatter plots on the object, which would complicate or make impossible the recording and registration of the geometry of the object in this area. In addition, this arrangement makes possible a very compact, in particular thin design.

Other preferred embodiments of the invention are subjects of the other subclaims.

BRIEF DESCRIPTION OF THE DRAWINGS

Other features and advantages of the invention follow from the description below of preferred embodiments of the invention with reference to the attached drawings.

Here:

FIG. 1 shows an embodiment of a handpiece for the invention from the side,

FIG. 2 shows the handpiece of FIG. 1 in top view,

FIG. 3 shows the handpiece of FIG. 1 from the front,

FIG. 4 shows the handpiece of FIGS. 1 to 3 in oblique view,

FIG. 5 shows a partial exploded view of an embodiment of the invention,

FIG. 6 shows a longitudinal section through the embodiment of FIG. 5,

FIG. 8 shows a section through the device along the line VIII-VIII, and

FIG. 9 shows a detail of an embodiment of a projector.

DETAILED DESCRIPTION OF THE PREFERRED EMBODIMENTS

Figure 7:
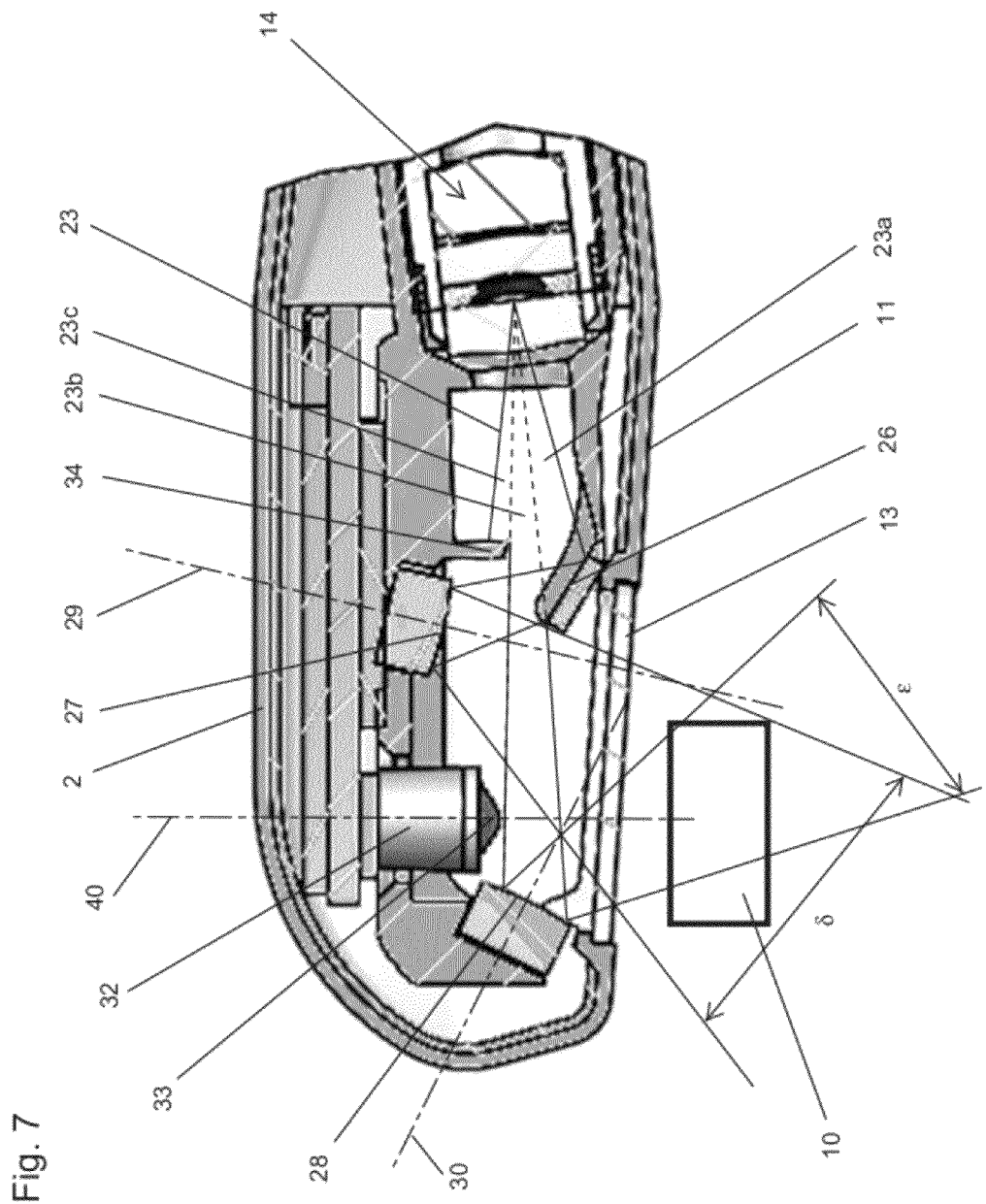
FIG. 7 shows a detail of FIG. 6.

In the drawings, a preferred embodiment of a device 1 for three-dimensional imaging of objects 10, in particular teeth, is shown, which has an imaging portion 2 and a gripping portion 3. Between the imaging portion 2 and the gripping portion 3, a central portion 5 is arranged in the embodiment depicted. Since the central portion 5 has a smaller outside dimension than the imaging portion 2, the imaging portion 2 has an essentially conical transition area 6 to the central portion 5. On the front end 4, the imaging portion 2 is rounded.

The imaging portion 2 has a center axis 7, the gripping portion 3 has a center axis 8, and the central portion 5 has a center axis 9. The angle $\alpha$ between the center axis 7 and the center axis 8 lies between 10° and 40° according to the invention, whereby this angle $\alpha$ in the embodiment depicted (with a central portion 5) is divided into two angles $\beta$ and $\gamma$, whereby the angle $\beta$ lies between the center axis 7 of the imaging part 2 and the center axis 9 of the central portion 5, and the angle $\gamma$ lies between the center axis 9 of the central portion 5 and the center axis 8 of the gripping part 3. The angle $\beta$ preferably lies between 3° and 15°, and the angle $\gamma$ lies between 7° and 25°. The length of the imaging area preferably lies between 10 and 60 mm, since within these limits, both a good manageability of the handpiece 1 and sufficient space for installing the projection and/or imaging technology is present.

On its side 11 that faces the object 10 that is to be imaged, an opening 12 (FIG. 5) is arranged in the imaging part 2, which is sealed by a disk 13. Through this disk 13, light, in particular a random pattern, can be directed onto the object 10 with a projector 14, and images of the object 10 can be recorded with a camera system 15. Relative to the gripping portion 3, the imaging portion 2 is thus tilted backward against the projection direction by an angle $\alpha$ of between 10° and 40°.

In FIGS. 5 to 8, an embodiment of the invention is depicted, in which the projector 14 irradiates a light beam 23 with a light source. The light beam 23 enters through one or more transparent vehicles 36, 37, depicted in FIG. 9, for example slides, on which a pattern, arranged according to a random principle, is arranged. The pattern preferably consists of essentially randomly distributed, optionally irregularly formed points and/or lines, which are subsequently projected onto the object 10, for example a tooth.

In the beam path of the light beam 23, there is a deflection mirror 26, which deflects one part 23a of the light beam 23, the lowermost part in the embodiment of FIG. 7, to a first mirror 27, which subsequently directs the light to the object 10. Another part 23b of the light beam 23, the central part in the embodiment of FIG. 7, strikes a second mirror 28 directly, from which the light is also directed to the object 10.

The deflection mirror 26 is preferably a flat mirror, but it could also be a convex or concave mirror, if necessary. The two mirrors 27 and 28 are preferably two-axis convex mirrors with the same or different radii of curvature in the two axes, with which the respective proportion of the ray beam 23 can be more greatly scattered, if necessary.

In the embodiment depicted, the arrangement and the curvature of the deflection mirror 26 and the first mirror 27 is selected in such a way that the part 23a of the light beam 23 in the image plane of the drawing has an opening angle $\delta$ of approximately 30°. By way of example, the arrangement and curvature of the second mirror 28 is selected in such a way that the part 23b of the light beam 23 in the image plane of the drawing has an opening angle $\epsilon$ of approximately 25°. The opening angle of parts 23a, 23b of the light beam 23 in a normal direction to the image plane of the drawing can be the same or different, depending on the requirement, in the respective opening angles $\delta$, $\epsilon$ lying in the image plane because of the suitable curvature of the mirrors 27, 28.

Because of the arrangement of the mirrors 27, 28 selected by way of example in FIG. 7, the optical axes 29, 30 of said mirrors are tilted toward one another in such a way that the light beam parts 23a, 23b strike the object 10 from different directions.

In the projection direction of the projector 14 viewed between the two mirrors 27, 28, in the embodiment depicted somewhat nearer to the second mirror 28, a camera system 15 is arranged, which in the embodiment depicted consists of two cameras 32, which record stereoscopic images for three-dimensional measurement of the object 10, by images being recorded from different directions with imaging areas that overlap one another. The two optical axes 29, 30 of the mirrors 27, 28 span a plane $\omega$, whereby the two cameras 32, more precisely their objectives 33, are symmetric to both sides of this plane $\omega$.

By this preferred arrangement, the camera system 15 lies with the mirrors 26, 27 or their optical axes 29, 30 in a plane $\omega$, which makes possible very precise image recording and thus measuring of the object. By the projection of the light beam parts 23a, 23b by mirrors 26, 27, which lie on both sides of the camera system 15, an illumination or projection of the random pattern onto the object 10 also takes place from two sides in this plane $\omega$, by which—viewed from the standpoint of the camera system 15—shadows or flaws on the object 10, which can occur, for example, in the case of molars or incisors, can be very reliably avoided.

In principle, it would also be possible to position the mirrors—viewed from the projector 14—in addition to the two cameras 32 and optionally to rotate the two cameras 32 by 90° so that they both lie in the plane $\omega$. More than two mirrors, both in front of and/or behind and lateral to the cameras 32, are also conceivable to produce the best possible illumination or pattern projection on the object 10.

In the embodiment depicted, in the area above the deflection mirror 26, an aperture 34 is arranged that blocks a third part 23c of the light beam 23 so that the latter does not cause any undesirable reflections in the optics 33 of the cameras 32. Depending on the arrangement of the mirrors 26, 27, 28 and the objectives 33, the aperture 34 can also be omitted or arranged or formed elsewhere.

All mirrors 26, 27, 28, the aperture 34, and optionally also the camera system 15 can be fastened in an adjustable manner to corresponding holding devices 31 so that if necessary, a simple adjustment and/or calibration of the individual components is possible. In addition, all or even only a portion of the above-described components can be fastened to a vehicle system and preadjusted, which then can be used in an imaging device. The housing of the device 1 preferably consists of two housing halves 16, 17, which are designed as a mirror image, by which the device can be assembled very easily.

By the selected arrangement according to the invention that is depicted by way of example in the drawing, a very compact and thin design is possible, which can be integrated, for example, very readily in a handpiece for three-dimensional imaging of teeth.

The arrangement of mirrors and cameras described in connection with FIGS. 5 to 8 is preferably used in handpieces with an angled imaging portion 2 and optionally central portion 5, since an especially good option is offered by the mirrors 26, 27, 28 to incorporate the entire projection and imaging technology into an angled handpiece 1, which is very thin and especially easily handled owing to the sharp bend in particular in the case of oral scanners.

In the device according to the invention, an optimal degree of sharpness can be achieved directly starting from the outside surface of the scanner glass 13 without the risk of shadows or flaws, and just by placing the scanner on an object, e.g., a tooth, the latter can be measured; conversely, known scanners often have to be held at a certain distance from the teeth, which significantly hampers the imaging process, in comparison to the possibility according to the invention of also being able to be placed directly on the teeth.

In FIG. 9, an embodiment of the invention is diagrammatically depicted in which two transparent vehicles 36, 37, for example two slides, on which patterns arranged according to a random principle are arranged, lie in the beam path of a light beam 23, which is irradiated from a light source 22, for example an LED. The pattern can essentially consist of randomly distributed, optionally irregularly formed points and/or lines. The light goes into the embodiment depicted first through a lens 35, then through the two vehicles 36, 37, and subsequently through another lens system that is symbolically depicted by a lens 38 and that is used to orient the projection beam 23 and to adjust sharpness.

The projector 14 of FIG. 9 can be used, for example, in a device that is depicted in FIGS. 5 to 8, in which the light beam 23 is directed via two mirrors 27 and 28 to an object 10. Since the light traverses paths of different lengths, depending on whether it strikes either via the deflection mirror 26 and the mirror 27 or via the mirror 28 on the object 10, blurring of one of the other or both projections can develop in the projection of the pattern, present on a vehicle, onto the object 10.

By using two vehicles 36, 37, this can be taken into account, and blurs can be compensated for individually. This can be done, for example, in that the two vehicles 36, 37 are offset with respect to one another in the propagation direction of the light. Thus, e.g., the vehicle 36, which lies in the beam path of the light beam 23b of the mirror 28, is further behind or further away from the lens 38 or a subsequent lens system than the vehicle 37, which lies in the beam path of the light beam 23a of the mirror 27 so that altogether, the path of the light from the respective vehicle 36, 37 via the respective mirror(s) 26, 27, 28 to the object 10 is again approximately the same length. The different distances from the vehicles 36, 37 to the lens system 38 are decisive, since these distances determine the position and location of the definition plane in the measuring space. If the path difference via the respective mirror(s) 26, 27, 28 to the object 10 is not very large, for example, also only a single vehicle could be used, which either has sections offset in stages or which is even, however, correspondingly greatly inclined to compensate for the path difference in the center. As another option, a single vehicle could also be used, which is coated with a pattern on different areas or sections in each case on the front side and on the back side. The thickness of the vehicle material then determines the distance difference.

In FIG. 9, a tilting of the vehicles 36, 37 relative to the propagation direction of the light can be seen, i.e., the vehicles 36, 37 are not exactly at a right angle relative to the propagation direction of the light. This embodiment of the invention is advantageous when the projector 14 or its optical center axis 39 as in the embodiment depicted in FIGS. 1 to 8 is oriented at an angle β that is greater than 0° in the imaging portion 2; in particular, the optical center axis 39 is not oriented at a right angle to the optical center axis 40 of the camera 32. The arrangement of the projector 14 in the angled transition area between the imaging portion 2, in which the camera 32 is located, and the central portion 5 is especially advantageous, since in this way, the imaging portion 2 can be kept relatively short, which significantly improves the handling of the handpiece 1. Blurring of the pattern projected onto the object 10 caused by tilting the projector 14 can be compensated for by tilting the vehicles 36, 37.

The invention claimed is:

1. A device for recording images of three-dimensional objects, the device comprising:
   a light source emitting a light beam stream including light beams;
   at least one camera configured to record images of each of the objects;
   at least one transparent vehicle arranged in the beam path of the light source having a pattern that is projected onto the object; and
   at least two mirrors each having positions that are different from one another, the light beams from the light source being directed to the object via the positionally-different mirrors,
   wherein parts of the light beams forming the pattern that is projected onto the object traverse paths of different lengths to the object to be imaged, and
   the transparent vehicle has sections that are offset with respect to one another in the direction of the beam path such that the length of each of the paths of the light beams forming the pattern from the transparent vehicle to the object is approximately the same length.

2. The device according to claim 1, wherein at least one of the vehicles is tilted at an angle that is not equal to 90° with reference to the propagation direction of the light.

3. The device according to claim 1, wherein at least two of the mirrors each reflect a light beam from the light source from different directions onto the object, and
   wherein a section of a vehicle or each separate vehicle lies in the beam path of each of the light beams.

4. The device according to claim 3, wherein the mirrors have differently oriented optical axes.

5. The device according to claim 4, wherein the optical axes of the mirrors lie in a plane.

6. The device according to claim 5, wherein the objectives of the cameras, viewed from the light source, are beside one another, and the objectives of the cameras are symmetric to the plane, in which the optical axes of the mirrors lie.

7. The device according to claim 3, wherein light is directed onto a first mirror indirectly via a deflection mirror, and light is directed onto a second mirror directly from the light source.

8. The device according to claim 3, wherein two of the mirrors lie on different sides of the camera.

9. The device according to claim 8, wherein, viewed from the light source, a first mirror lies in front of an objective of the camera and a second mirror lies behind the objective.

10. The device according to claim 1, wherein the at least one camera includes two cameras with imaging areas that overlap one another and that record images from different directions.

11. The device according to claim 10, wherein objectives of the cameras, viewed from the light source, are beside one another.

12. The device according to claim 1, wherein the light source projects a pattern, arranged according to a random principle, onto the object.

13. The device according to claim 12, wherein the pattern essentially consists of randomly distributed, irregularly formed points and/or lines.

14. The device according to claim 1, further comprising
an imaging portion, in which the mirrors are arranged; and
a gripping portion,
  wherein the camera and/or the light source is/are arranged in the imaging portion, and
  wherein the imaging portion is tilted against the projection direction by an angle of between 10° and 40° relative to the gripping portion.

15. The device according to claim 14, wherein a central portion, which is tilted relative to each of the gripping portion and the imaging portion by an angle of at least 3°, is arranged between the gripping portion and the imaging portion.

16. The device according to claim 14, wherein the central portion is tilted relative to the gripping portion by an angle ($\gamma$) of 7° to 25°.

17. The device according to claim 14, wherein the imaging portion is tilted relative to the central portion by an angle of 3° to 15°.

18. The device according to claim 14, wherein in the transition area, the light source is arranged between the imaging portion and the central portion or gripping portion behind the imaging portion.

19. The device according to claim 1, wherein the three-dimensional objects are teeth.

20. A device for recording images of three-dimensional objects, the three-dimensional objects being teeth, the device comprising:
  a light source emitting a light beam stream including light beams;
  a camera configured to record images of each the objects;
  at least two transparent vehicles each arranged in the beam path of the light source having a pattern that is projected onto the object,
  at least two mirrors each having positions that are different from one another, the light beams from the light source being directed to the object via the positionally-different mirrors,
  wherein parts of the light beams forming the pattern that is projected onto the object traverse paths of different lengths to the object to be imaged, and
  at least two of the vehicles are offset with respect to one another in the direction of the beam path such that the length of each of the paths of the light beams forming the pattern from the transparent vehicle to the object is approximately the same length.

21. The device according to claim 20, wherein at least one of the vehicles has sections that are offset with respect to one another in the direction of the beam path.

22. The device according to claim 20, wherein the three-dimensional objects are teeth.

* * * * *